(12) United States Patent (10) Patent No.: US 9,115,776 B2
Chung et al. (45) Date of Patent: Aug. 25, 2015

(54) FLEXING ARRANGEMENT

(71) Applicant: CITY UNIVERSITY OF HONG KONG, Kowloon (HK)

(72) Inventors: Chi Yuen Chung, Kowloon Tong (HK); Lok Wang Ma, Kowloon (HK)

(73) Assignee: CITY UNIVERSITY OF HONG KONG, Hong Kong (HK)

( * ) Notice: Subject to any disclaimer, the term of this patent is extended or adjusted under 35 U.S.C. 154(b) by 217 days.

(21) Appl. No.: 13/680,410

(22) Filed: Nov. 19, 2012

(65) Prior Publication Data

US 2014/0142482 A1 May 22, 2014

(51) Int. Cl.
*A61F 5/00* (2006.01)
*F16F 3/02* (2006.01)
*A61F 5/01* (2006.01)
*A61F 5/055* (2006.01)

(52) U.S. Cl.
CPC ............... *F16F 3/023* (2013.01); *A61F 5/013* (2013.01); *A61F 5/0123* (2013.01); *A61F 5/055* (2013.01); *A61F 2005/0169* (2013.01); *Y10T 16/538* (2015.01)

(58) Field of Classification Search
CPC ....... A61F 2/2493; A61F 2/2412; A61F 2/24; A61F 2/966; A61F 2/95; A61F 2002/30331; A61F 2002/3037; A61F 2002/30387; A61F 2002/30397; A61F 2002/30398; A61F 2002/304; A61F 2002/30507; A61F 2002/30

USPC .................. 602/16, 23–28; 128/882
See application file for complete search history.

(56) References Cited

U.S. PATENT DOCUMENTS

| | | | |
|---|---|---|---|
| 4,191,053 A * | 3/1980 | Hart et al. | 374/112 |
| 4,524,764 A | 6/1985 | Miller | |
| 5,823,931 A | 10/1998 | Gilmour | |
| 6,718,656 B2 | 4/2004 | Houser et al. | |
| 6,773,411 B1 | 8/2004 | Alvarez | |
| 7,063,531 B2 * | 6/2006 | Maijer et al. | 433/11 |
| 7,597,675 B2 | 10/2009 | Ingimundarson et al. | |
| 2008/0140202 A1 * | 6/2008 | Allard et al. | 623/17.13 |
| 2012/0203345 A1 * | 8/2012 | Voorhies | 623/17.16 |

FOREIGN PATENT DOCUMENTS

| | | |
|---|---|---|
| AU | 2005/306586 B2 | 5/2006 |
| WO | WO2006/053391 A1 | 5/2006 |
| WO | WO2010/088716 A1 | 8/2010 |

* cited by examiner

*Primary Examiner* — Michael Brown
(74) *Attorney, Agent, or Firm* — Heslin Rothenberg Farley & Mesiti P.C.; Melvin S. Li (57) ABSTRACT

The present invention is concerned with a flexing arrangement with a wide range of applications. The arrangement has at least one leaf spring structure having a plurality of reusable leaf springs connected together. At least one of the leaf springs is made of essentially of an alloy of nickel and titanium, and the alloy has a nickel content of substantially 50.1-55 at % and a titanium content of substantially 45-49.9 at %.

18 Claims, 14 Drawing Sheets

FLEXING ARRANGEMENT

FIELD OF THE INVENTION

The present invention is concerned with a flexing arrangement with a wide range of applications. The flexing arrangement may be applied to knee supports, ankle supports, medical devices or the like, or in the construction industry.

BACKGROUND OF THE INVENTION

The use of knee support brace or sleeve in patients with patellofemoral pain has increased tremendously in recent years. Statistics have shown that taping the patella into a certain position to reduce friction may be helpful. However, the patellofemoral mechanism is complicated, for the patella moves in several planes. Accordingly, seeking to adjust the position of the patella is not always reliable or predictable. Further, the design or materials used in conventional knee supports, and the mechanism by which these knee supports behave or interact with the knees, are not well understood.

There are a variety of conventional knee supports. One characteristic shared by many of such supports are that they are made of steel- or stainless steel-type material. The advantage of using such supports with steel-typed material is that they can provide strength or good support. However, such supports often suffer from various drawbacks including poor flexibility, etc.

The present invention seeks to provide a flexing arrangement or the like which can be used in a wide range of applications including but not limited medical or rehabilitation support structures, or at least to provide an alternative to the public.

SUMMARY OF THE INVENTION

According to a first aspect of the present invention, there is provided a flexing arrangement comprising at least one supporting structure including a plurality of reusable leaf springs connected together, at least one of said leaf springs is made of essentially of an alloy of nickel and titanium, wherein the alloy has a nickel content of substantially 50.1-55 at % and a titanium content of substantially 45-49.9 at %. The leaf springs may be elongate in shape and configured to resemble strips.

In an embodiment, the flexing arrangement may be configured to take the form of a supporting brace or sleeve for medical or rehabilitating use. The supporting brace or sleeve may be a knee supporting device for assisting patients with patellorfemoral pain syndrome (PFPS). The supporting brace or sleeve may be a device for assisting users or patients with problems in the elbow joint, neck or back.

Preferably, the width, length and thickness of the one leaf spring may range from substantially 9-11 mm, 270-330 mm and 0.9-1.1 mm, respectively, or 10 mm, 300 mm and 1 mm, respectively. The one leaf spring may range from substantially 13.5-16.5 g or 15 g in weight. The flexing arrangement may comprise 10 leaf springs.

The leaf spring may be adapted to provide a supporting force 40 times of its weight. The leaf spring may be adapted to provide a supporting force of substantially 540-660 or 600 g.

In one embodiment, one leaf spring may be adapted to assume a first configuration in which an angle of bending of the leaf spring is less than 30° and a second configuration in which the angle of bending of the leaf spring is 30-170°, and wherein in either configuration the one leaf spring is adapted to resume complete recovery after bending without plastic deformation after unloading. The leaf spring when in the second configuration may be adapted to provide a substantially uniform recoil force across the bending angle from 30-170°.

According to a second aspect of the present invention, there is provided a medical accessory device comprising a flexing arrangement as described. The device may be a knee support with a weight ranging from substantially 765-935 g or 850 g.

According to a third aspect of the present invention, there is provided a constructional component comprising a flexing arrangement as described above. The component may act as a damping device for absorbing force or reducing speed of a movable member. The constructional component may reside in or be used in association with a door hinge.

BRIEF DESCRIPTION OF THE DRAWINGS

Some embodiments of the present invention will now be explained, with reference to the accompanied drawings, in which.

DETAILED DESCRIPTION OF PREFERRED EMBODIMENTS OF THE INVENTION

By way of background, orthopedic support braces and devices have been widely applied for the major articulated joints of the body including the neck, elbow, wrist, hip, knee, ankle, etc. in recent years. These passive orthopedic support braces are designed to protect injured joints, and joints undergoing rehabilitation as well as any other type of weakened joints.

For example, patellofemoral pain syndrome (PFPS) is one of the most common disorders of knee and affects one in four people. Basically, it is a retropatellar or peripatellar pain resulting from physical and biochemical changes in the patellofemoral joint. Patients with patellofemoral pain syndrome have anterior knee pain that typically occurs with sports or daily activities, and as is exacerbated by stair climbing. It can also be triggered by prolonged sitting.

Figure 1:
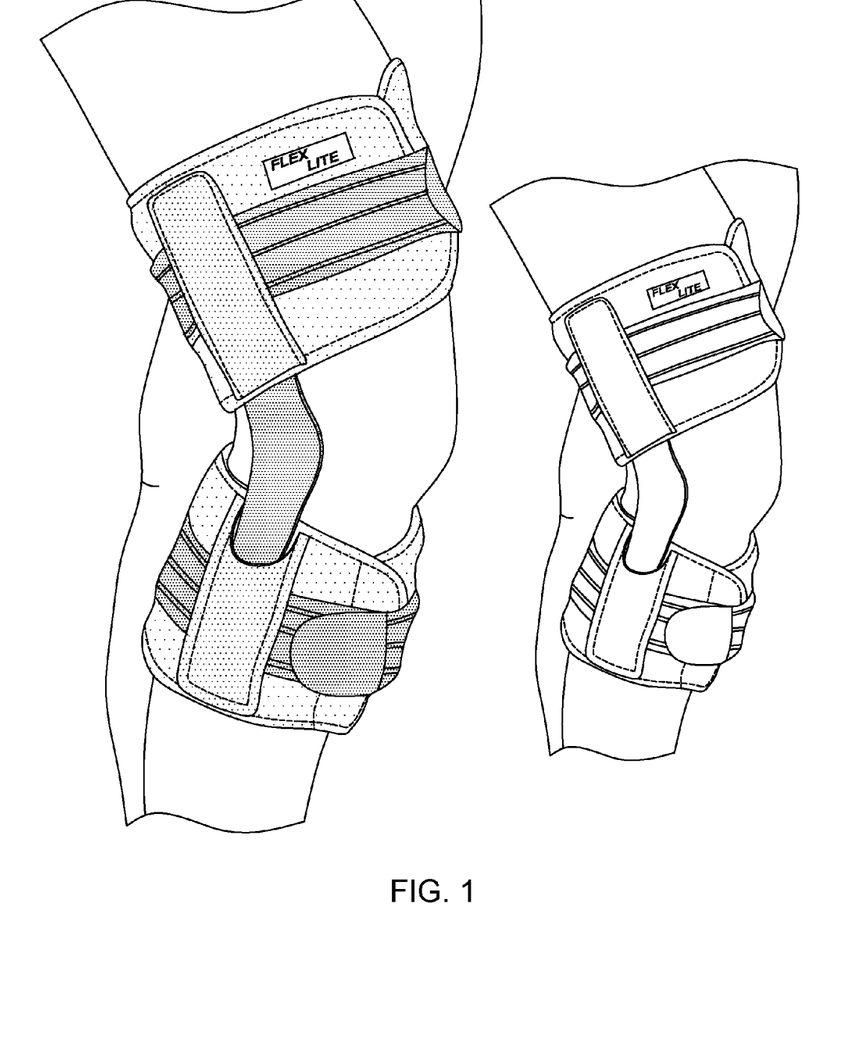
FIG. 1 is a photographic representation of a knee support.

A variety of knee support braces and sleeves were extensively designed by different manufacturers and suppliers, for helping patients with patellofemoral pain syndrome (PFPS). For example, light alloys, such as aluminum and magnesium or carbon composite were used to reduce the weight of the brace. Stainless steels were used to increase the strength and durability and hinge was also added for flexion or extension stops with different degrees. FIG. 1 shows a typical design of hinged knee support for PFPS patient. However, the use of these passive support braces/sleeves may result in a reduction in power generation at the joints; they limit active plantar flexion. Moreover, these braces may lead to disuse atrophy of the muscles, such as the tibialis anterior muscle, potentially leading to long-term dependence.

The use of stainless steel as a material for constructing a supporting structure in, for example, a knee support suffers the drawback of its stiffness and inflexibility. It follows that movement of a user of such knee support is severely restricted. Further, the flexing behavior of a stainless steel supporting structure is deficit because regardless of the degree of bending of the supporting structure the recoil force from the supporting structure is relatively constant. This would cause undesirable reliance on the use of such support and defeat the purpose of rehabilitation by using the structure.

Research leading to the present invention has identified that alloy of nickel-titanium (NiTi) is a desirable candidate for use in such supporting structure or flexing structure in general. NiTi alloy possesses a super-elastic (SE) property and can act as a shape memory alloy (SMA). In other words, NiTi alloy can be considered as a smart material with greater flexibility than any, or at least many, other metallic materials. The elastic strain of the NiTi SMA is approximately of 10-20 times greater than that of stainless steel. Accordingly, by applying NiTi SMA in support or flexing mechanism in, for example, knee support brace, sleeve or the like the behavior of such support can be much improved. Specifically, the NiTi SMA may be embedded in the support by way of introducing super-elastic NiTi SMA wires, rods or leaf springs. The use of such support mechanism in the context of super-elastic knee brace/sleeve is able to provide sufficient support and/or resistance against the flexure of the joint by adjusting the cross section and dimension of NiTi SMA wires, rod(s) or bar(s) and yet bending of the knee joint motion will not be unduly restrained. In other words, the present invention can be applied in the context of medical or rehabilitation of joints (knee, ankle, back, etc.), and such medical or rehabilitation devices are able to provide sufficiently strong support to the weakened joints but without substantially limiting the flexibility of the joint or causing reliance of the joints on the devices.

The high recoverable elastic strain, low elastic modulus, and high corrosion resistance have made NiTi SMA unique among other metallic materials. Support mechanism made with super-elastic NiTi shape memory alloy (SMA) members (e.g. wires, leaf springs, etc.) can be achieved by embedding the members within a soft material. In this manner, the support can provide variable assistance depending on the gait cycle phase, activity level, and needs of the wearer. As a result, the wearer can have individualized control, causing the muscles to be used more appropriately.

Figure 2:
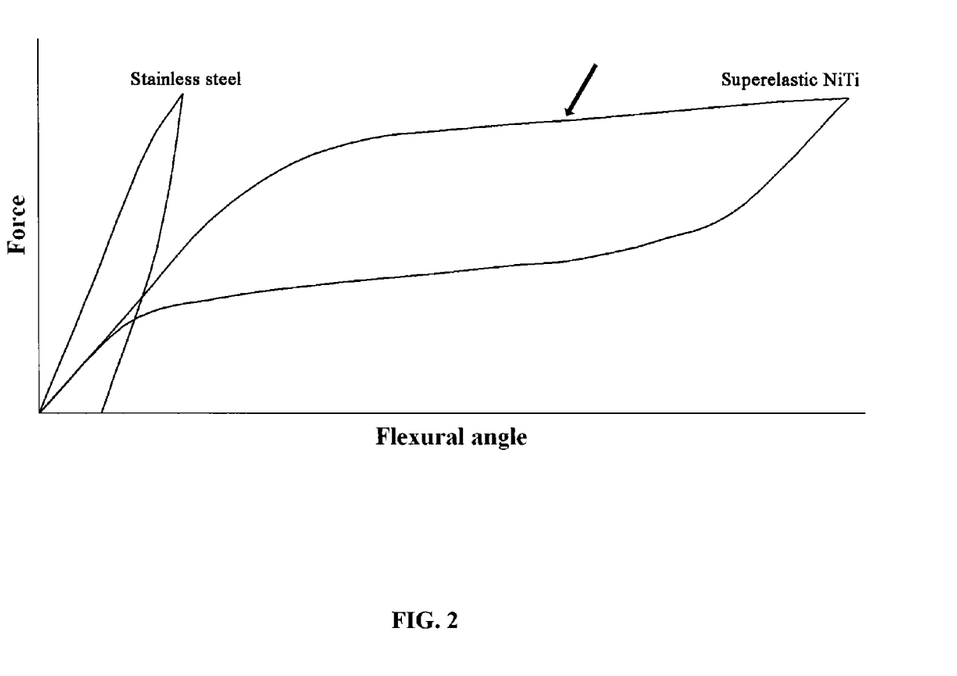
FIG. 2 is a graph schematically showing force-flexural angle curves of stainless steel rod and super-elastic NiTi SMA rod.

Experiments were performed to study the behavior of a novel super-elastic flexing arrangement in the context of a knee support. Specifically, in one experiment super-elastic NiTi SMA wires/rods were used to study the supporting force against the flexural angle. In this experiment, a conventional three-point bending test was performed to compare the force against bending angle between stainless steel rod and super-elastic NiTi SMA rod. Please see FIG. 2. In FIG. 2, the force-flexural angle curves of stainless steel rod and super-elastic NiTi SMA rod, which were subjected to three-point being test, are shown schematically. Both rods had the same dimensions with about 6 mm in diameters and about 80 mm in length. From FIG. 2, it can be understood that when a stainless steel supporting structure is being flexed the force generated is generally proportional to the flexural angle, as indicated by the relatively straight and steep curves on the left side of the graph. To the contrary, when a NiTi supporting structure in according to an embodiment of the present invention is being flexed, the behavior of the structure generally falls into two relatively phases, a first phase in which the force generated is generally proportional to the flexural angle, and a second phase in which the force generated is relatively constant to the flexural angle.

Figure 3:
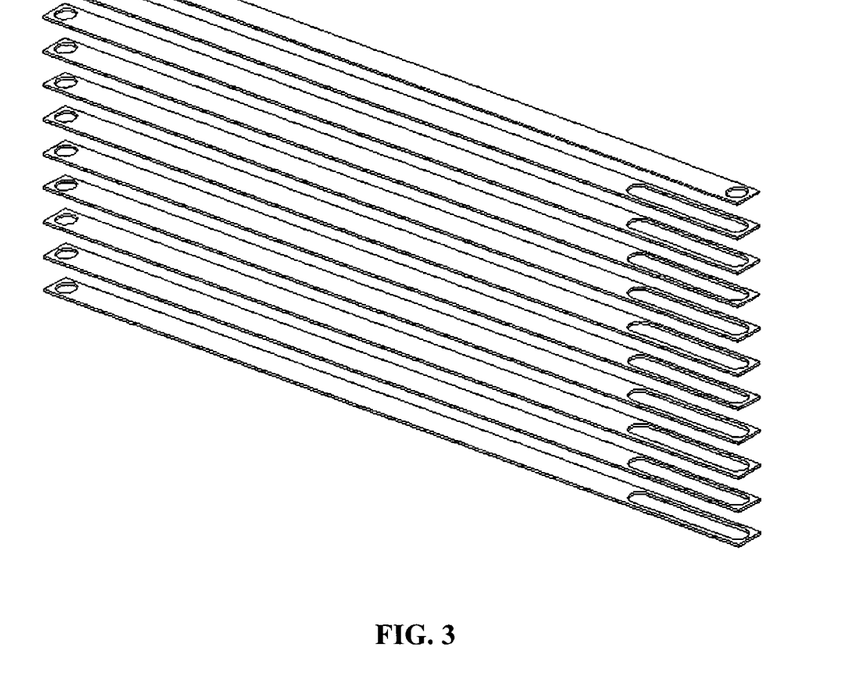
FIG. 3 is a schematic view of a plurality of leaf springs of a supporting structure according to an embodiment of the present invention.
Figure 4:
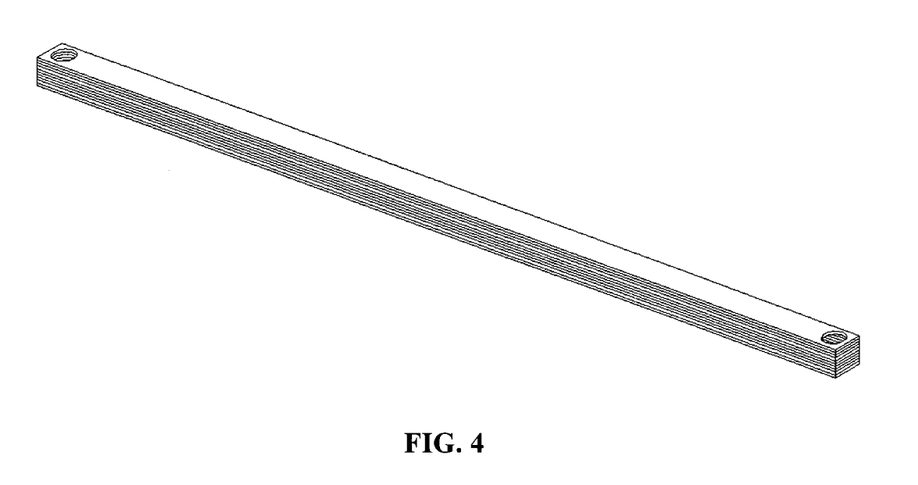
FIG. 4 is a perspective view of the leaf springs similar to FIG. 3 but with the leaf springs positioned adjacent to each other.
Figure 5:
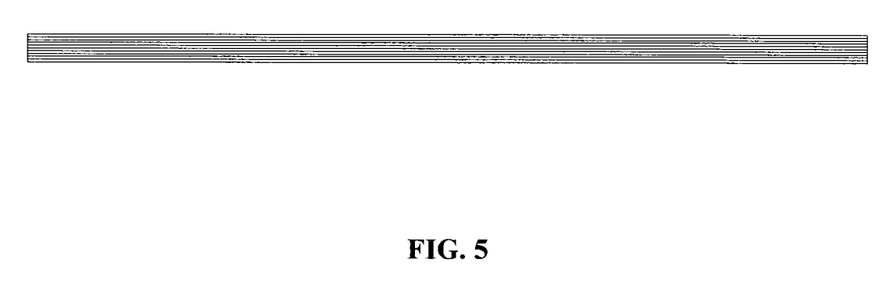
FIG. 5 is a side of the leaf springs of FIG. 4.
Figure 6:
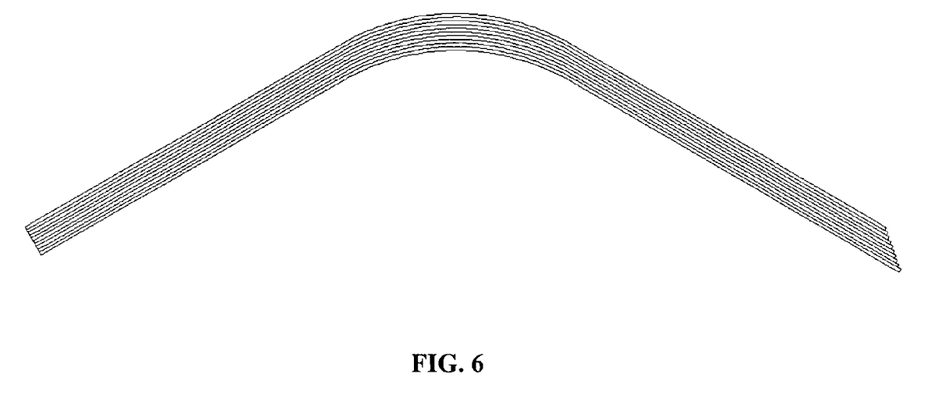
FIG. 6 is a side of the leaf springs of FIG. 5 but assumed in a different configuration.

FIG. 3 illustrates a number of NiTi members in the form of leaf springs which can be used in a knee support. FIGS. 4-5 is the NiTi members positioned adjacent each other. Opposite distal ends of the leaf springs are provided with openings aligned with each other. In use, a connection member is installed at the opening for assembling the springs which are then embedded in the knee support. FIG. 6 illustrates the profile when the connected leaf springs are subjected to flexural.

Figure 7:
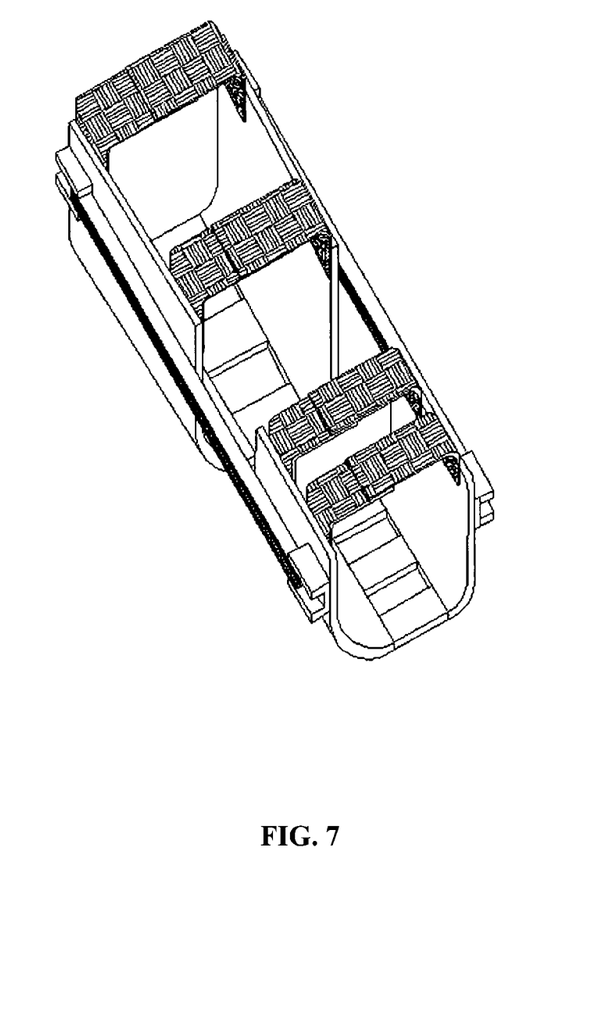
FIG. 7 is a perspective view of an embodiment of a knee support according to an embodiment of the present invention.

FIG. 7 illustrates an embodiment of knee support installed with such leaf springs.

Figure 8:
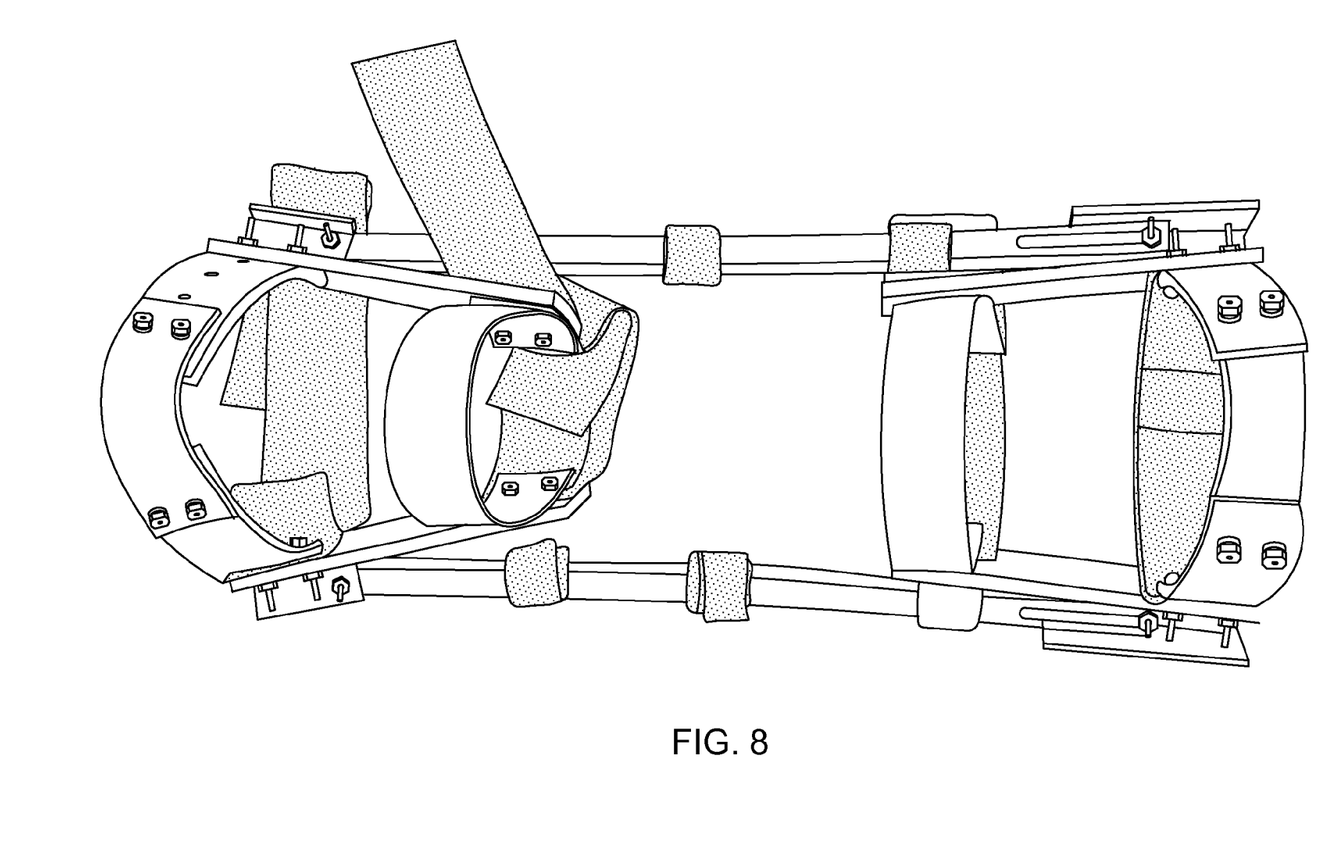
FIG. 8 is a photographic representation of another knee support.

FIG. 8 illustrates another embodiment of knee support installed with such leaf springs. In this embodiment, the total weight of the knee support is approximately 0.85 kg, with 10 NiTi plates arranged on each side of the knee support. In other words, there are 20 NiTi plates in total.

Figure 9:
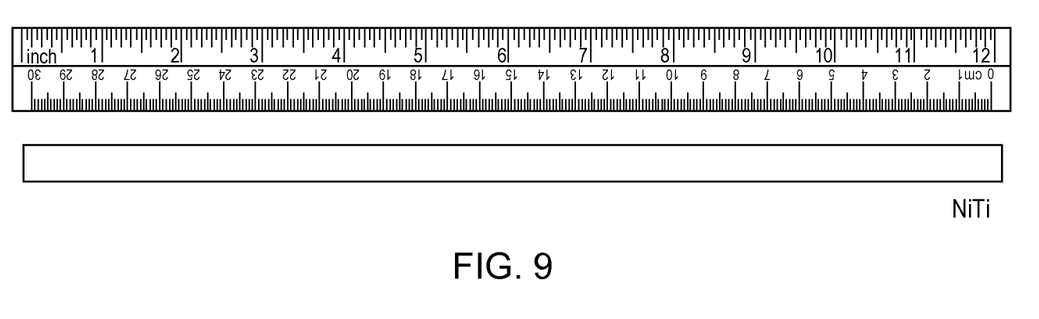
FIG. 9 is a photographic representation of one of the leaf springs shown in FIG. 3.

FIG. 9 illustrates the dimension and weight of one of the NiTi plates. The following table summarizes the dimension and weight of the NiTi plate.

TABLE 1

| Dimension and weight of a NiTi plate | |
|---|---|
| Dimension W × L × t (mm) | Weight (Kg) |
| 10 × 300 × 1 | 0.015 |

Figure 10:
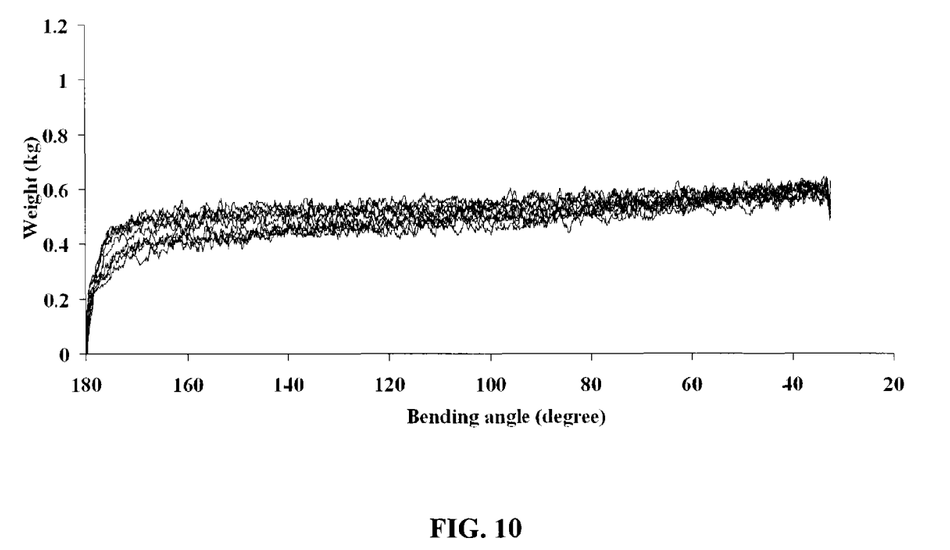
FIG. 10 is a graph with a curve illustrating the relationship between force and bending angle of a NiTi leaf spring according to an embodiment of the present invention.

FIG. 10 shows the force-bending angle curve of a NiTi plate according to an embodiment of the present invention. As illustrated, the maximum supporting force is ~0.6 kg which means each NiTi plate can support about 0.6 kg when loaded (bending angle from 180° down to ~30°). The force provided corresponds to 40 times of the weight of the NiTi plate. Unique plateau behaviour of the NiTi alloy, as shown the be straight dotted line marked by the arrow, showed almost uniform recoil force between ~30° and 170° deflections allowing more flexibility. Also, complete recovery (super-elasticity) with minimal plastic deformation or without any plastic deformation was obtained after unloading.

Figure 11:
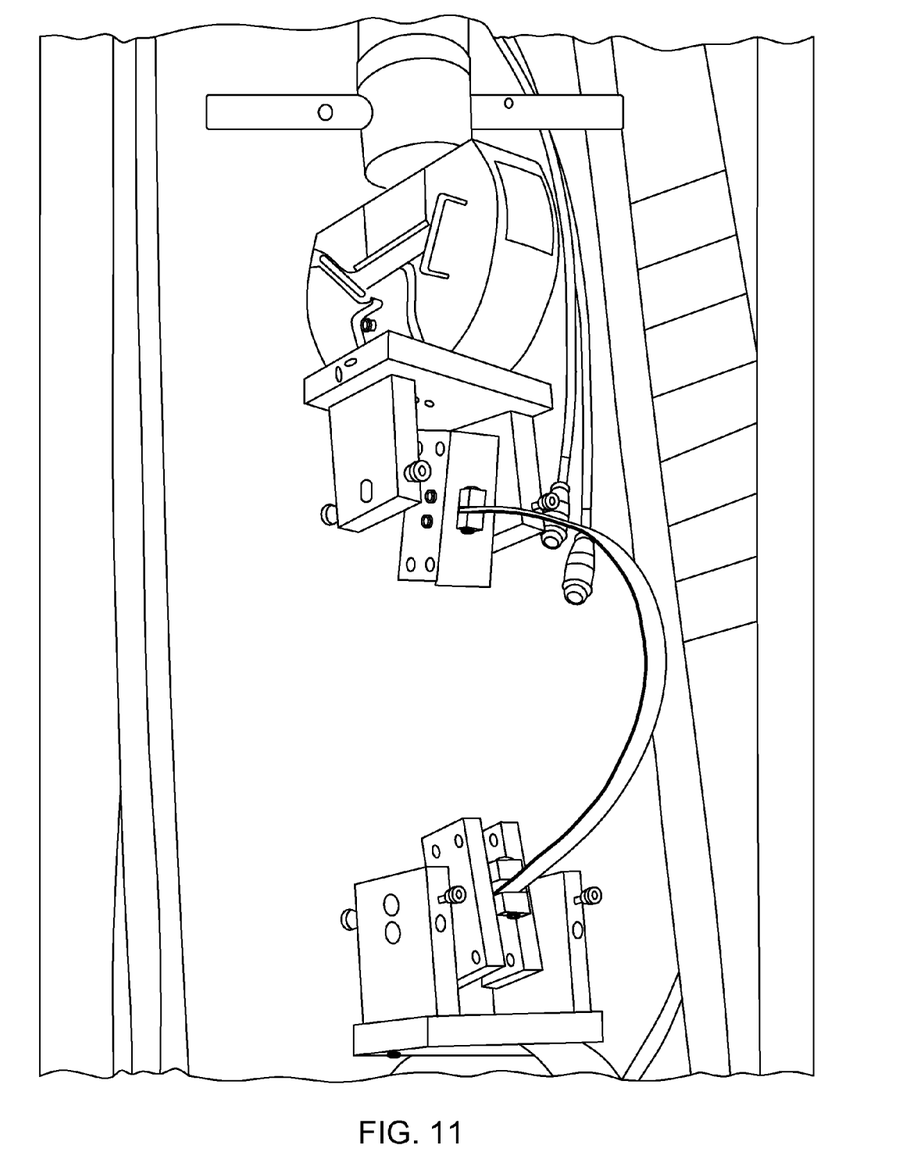
FIG. 11 is a photographic representation showing an embodiment of the NiTi leaf spring subject to experimental of loading and bending.

FIG. 11 shows the maximum bending angle (~40°) of the NiTi plate under loading. It should be noted that 180° of the NiTi plate refers to the condition of a straight plate without any loading.

Figure 12:
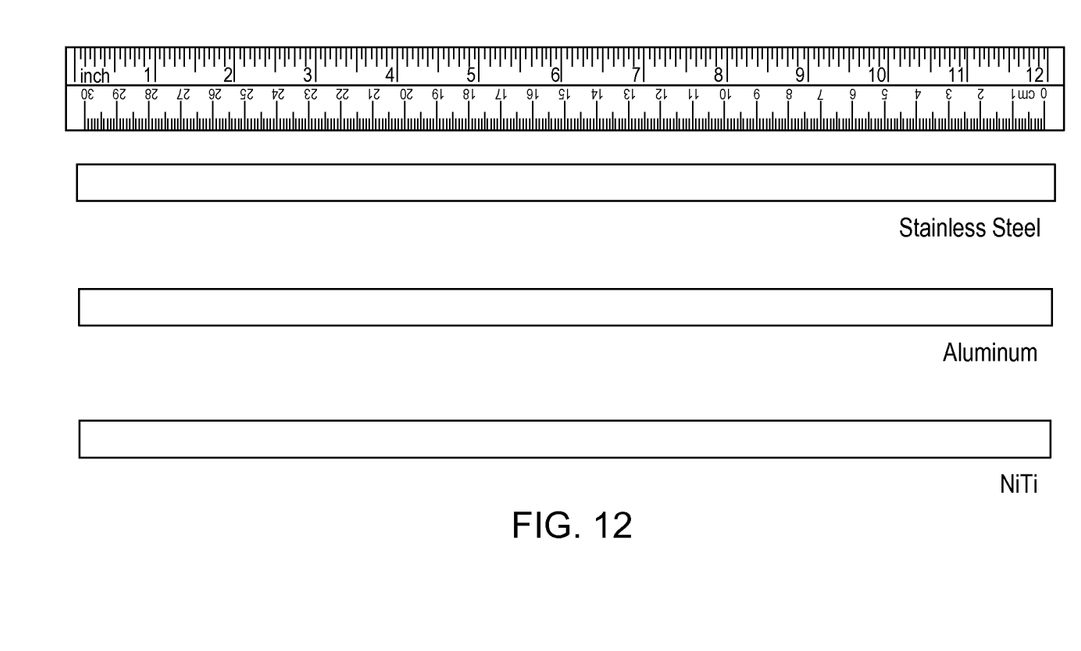
FIG. 12 is a photographic representation showing two leaf springs made of stainless steel and aluminum, and the leaf spring of NiTi alloy of FIG. 11.
Figure 13A:
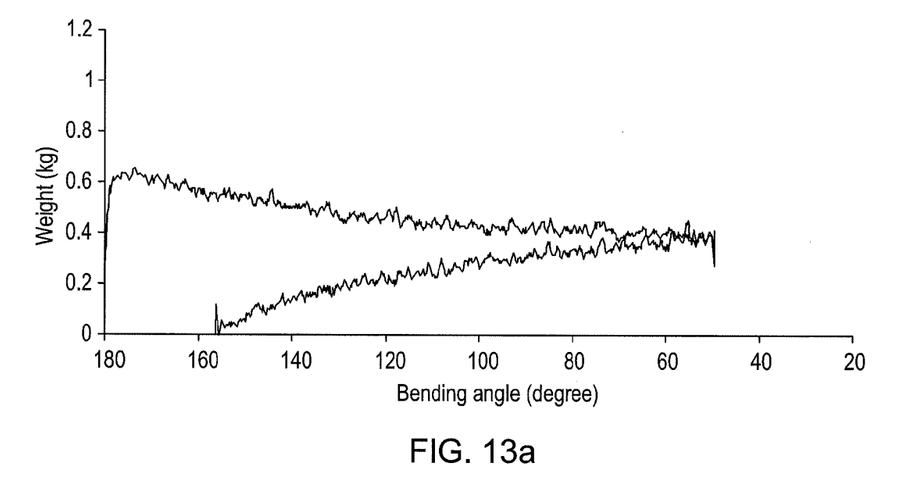
FIGS. 13a-b are graphs showing the relationship of bending angle and weight, in the context of the supporting structure being aluminum and stainless steel, respectively.
Figure 13B:
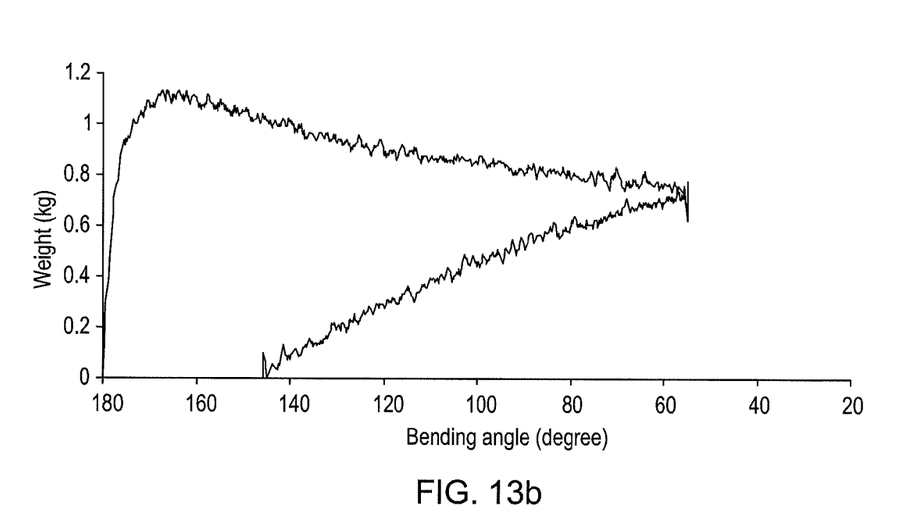
Figure 14:
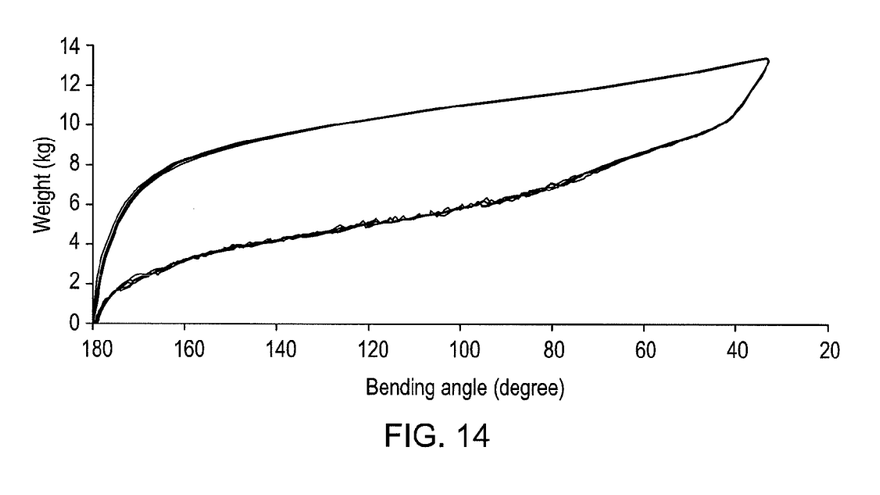
FIG. 14 is a graph showing the relationship of bending angle and weight, in the context of the supporting structure being a NiTi alloy.

With a view to compare the performance with the NiTi plate, two other plates (with the same dimensions) using aluminium and stainless steel materials were also tested. FIG. 12 shows a picture of three plates using NiTi, aluminium and stainless steel, respectively. FIG. 13 shows the force-bending angle curves of a) aluminium plate and b) stainless steel plate. When compared with FIG. 10, it can be seen that incomplete recovery behaviours, i.e. permanent plastic deformation, were found in both aluminium and stainless steel plates after unloading. Typical permanent plastic deformation behaviours can be observed in both curves. The supporting force was initially increased with bending angle from 180° to ~170°. However, the supporting force decreased with bending angle from ~170° to ~50°. This means the knee support cannot maintain the constant recoil/supporting force when using these two materials. Furthermore, the aluminium and stainless steels plates cannot be reused. To the contrary, the structure made of NiTi alloy able to recover, allowing it be re-used.

FIG. 7 shows the force-bending angle curve of 20 NiTi plates. The maximum supporting force is ~12 kg when bending all plates to ~35°. Therefore, the maximum supporting force is ~24 kg if two knee supports are used (using 40 NiTi plates).

Studies have shown that workable contents of the nickel-titanium (Ni—Ti) containing alloy members, as exemplified in the aforementioned experiments, may range from substantially 50.1-55 at % and 45-49.1 at %, respectively.

As illustrated above, a knee support made in accordance with present invention can produce a number of advantages. The technical results shown above have demonstrated the potential of the knee support in helping elderly or injured people with weakened knee joints or sport related injuries, etc. The invention can however be applied to other support devices including supports for the ankles, elbow, back, neck, etc. Modifications of such devices can be made to tailor to specific needs of individuals. For example, lighter and more advanced support device by means of weight, number of plates, length of plates, etc. can be tailor-made for different users with different needs.

The application of the present invention is not limited to medical or rehabilitation accessories. For example, the present invention can be applied to training devices for athletes and military personnel, for enhancing training efficiency.

Yet further, the present invention can be applied in the construction industry. For example, damping devices incorporating flexing members made with NiTi will provide control to movable members, e.g. door hinges.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose.

The invention claimed is:

1. A flexing arrangement comprising at least one leaf spring structure including a plurality of reusable leaf springs connected together, at least one of said leaf springs is made of essentially of an alloy of nickel and titanium, wherein the alloy has a nickel content of substantially 50.1-55 atomic % and a titanium content of substantially 45-49.9 atomic %.

2. A flexing arrangement as claimed in claim 1, wherein the flexing arrangement is configured to take the form of a supporting brace or sleeve for medical, rehabilitating or training use.

3. A flexing arrangement as claimed in claim 2, wherein the supporting brace or sleeve is a knee supporting device for assisting patients with patellorfemoral pain syndrome (PFPS).

4. A flexing arrangement as claimed in claim 2, wherein the supporting brace or sleeve is a device for assisting users or patients with problems in the elbow joint, neck or back.

5. A flexing arrangement as claimed in claim 1, wherein the width, length and thickness of said at least one leaf spring range from substantially 9-11 mm, 270-330 mm and 0.9-1.1 mm, respectively.

6. A flexing arrangement as claimed in claim 5, wherein the width, length and thickness of said at least one leaf spring are substantially 10 mm, 300 mm and 1 mm, respectively.

7. A flexing arrangement as claimed in claim 1, wherein said at least one leaf spring ranges from substantially 13.5-16.5 g.

8. A flexing arrangement as claimed in claim 7, wherein said at least one leaf spring is substantially 15 g in weight.

9. A flexing arrangement as claimed in claim 3, comprising 10 said leaf springs.

10. A flexing arrangement as claimed in claim 1, wherein said at least one leaf spring is adapted to provide a supporting force 40 times of the weight of said at least one leaf spring.

11. A flexing arrangement as claimed in claim 1, wherein said at least one leaf spring is adapted to provide a supporting force of substantially 540-660 or 600 g.

12. A flexing arrangement as claimed in claim 1, wherein said at least one leaf spring is adapted to assume a first configuration in which an angle of bending of the leaf spring is less than 30° and a second configuration in which the angle of bending of the leaf spring is 30-170°, and wherein in either configuration said at least one leaf spring is adapted to resume complete recovery after bending without plastic deformation after unloading.

13. A flexing arrangement as claimed in claim 12, wherein said at least one leaf spring when in the second configuration is adapted to provide a substantially uniform recoil force across the bending angle from 30-170°.

14. A medical accessory device comprising a flexing arrangement as claimed in claim 1.

15. A device as claimed in claim 1, wherein the device is a knee support with a weight ranges from substantially 765-935 g or 850 g.

16. A constructional component comprising a flexing arrangement as claimed in claim 1.

17. A constructional component as claimed in claim 16, wherein said component acts a damping device for absorbing force or reducing speed of a movable member.

18. A constructional component as claimed in claim 17, wherein said component resides in or is used in association with a door hinge.

* * * * *